United States Patent [19]
Williamson

[11] Patent Number: 5,277,699
[45] Date of Patent: Jan. 11, 1994

[54] FOOT DROP ORTHOTIC AND GAIT TRAINING DEVICE

[76] Inventor: Theodore A. Williamson, 16248 McKinley Road, Umatilla, Fla. 32784

[21] Appl. No.: 896,604
[22] Filed: Jun. 10, 1992
[51] Int. Cl.⁵ .......................... A61F 5/00; A61F 5/37
[52] U.S. Cl. ...................................... 602/28; 128/882
[58] Field of Search .................. 602/3, 23, 24, 26, 27, 602/28, 62, 65; 128/882; 273/55

[56] References Cited

U.S. PATENT DOCUMENTS

| | | | |
|---|---|---|---|
| 1,402,282 | 1/1922 | Chevrier | 602/28 |
| 2,531,486 | 11/1950 | Weber | 602/28 |
| 2,536,454 | 1/1951 | McIntyre | 602/28 |
| 2,584,010 | 1/1952 | Goffredo | 128/80 |
| 3,527,202 | 9/1970 | Donzelle | 128/1 |
| 3,527,209 | 9/1970 | Baker | 602/28 |
| 3,713,437 | 1/1973 | Wiedmer | 602/28 |
| 3,741,203 | 6/1973 | Liman | 602/3 |
| 3,986,501 | 10/1976 | Schad | 128/20 |
| 4,102,337 | 6/1978 | Golia | 602/28 |
| 4,329,982 | 5/1982 | Heaney | 128/80 |
| 4,566,447 | 1/1986 | Deis | 602/28 |
| 4,790,300 | 12/1988 | Marx | 128/84 |
| 4,817,589 | 4/1989 | Wertz | 602/28 |
| 4,949,711 | 8/1990 | Gyovai et al. | 128/87 |
| 4,955,370 | 9/1990 | Pettine | 128/80 |
| 5,139,479 | 8/1992 | Peters | 602/27 |

Primary Examiner—Michael A. Brown
Attorney, Agent, or Firm—Oltman and Flynn

[57] ABSTRACT

An appliance for stretching a pathologically contracted Achilles' wrist tendons includes a resilient strap having a first end and a second end, a harness for securing around the leg of a user, a fastener for attaching the first end of the resilient strap to a shoe so that the resilient strap extends out from the front of the shoe, and a fastener for attaching the second end of the resilient strap to the harness so that the resilient strap is bowed against its resilient resistance over the front of the shoe. A channel for receiving the first end of the resilient strap is preferably recessed into the bottom of the shoe. The harness preferably includes a securing strap and a foam rubber pad having an inner surface which rests against the leg of the user and having an outer surface to which the securing strap is attached. The harness may additionally include nylon fabric attached to the outer surface of the pad, and cotton fabric attached to the inner surface of the pad. The securing strap is preferably fitted with several ring members and the second end of the resilient strap has a clasp which removably engages a ring member to select the desired tension of the resilient strap. Also optionally provided is a high friction strip of material sized to fit into the channel for securing over the resilient strap first end to enhance the friction grip between the shoe and the ground.

12 Claims, 6 Drawing Sheets

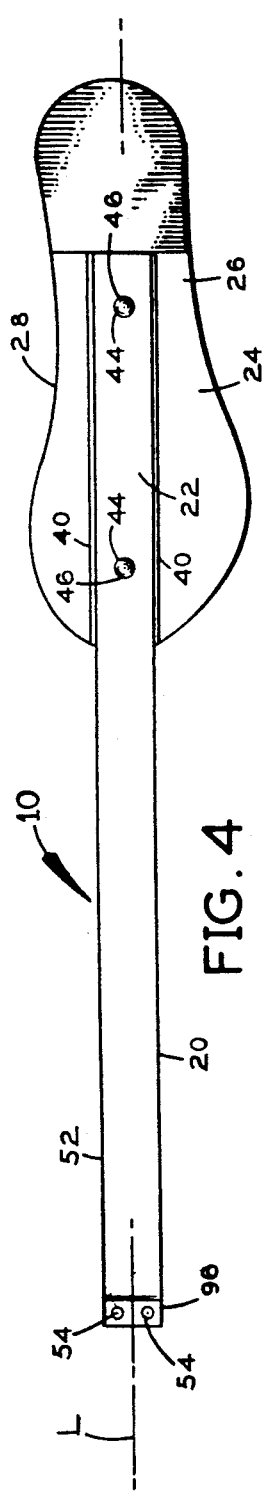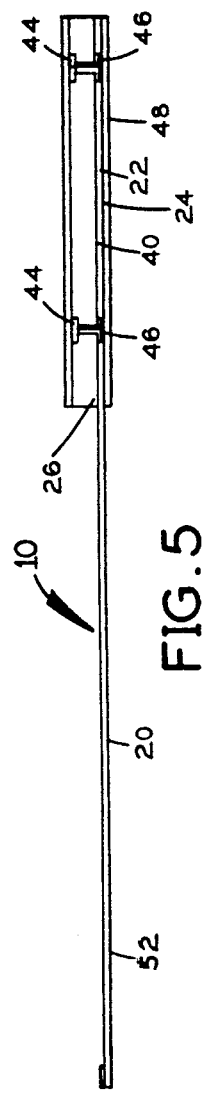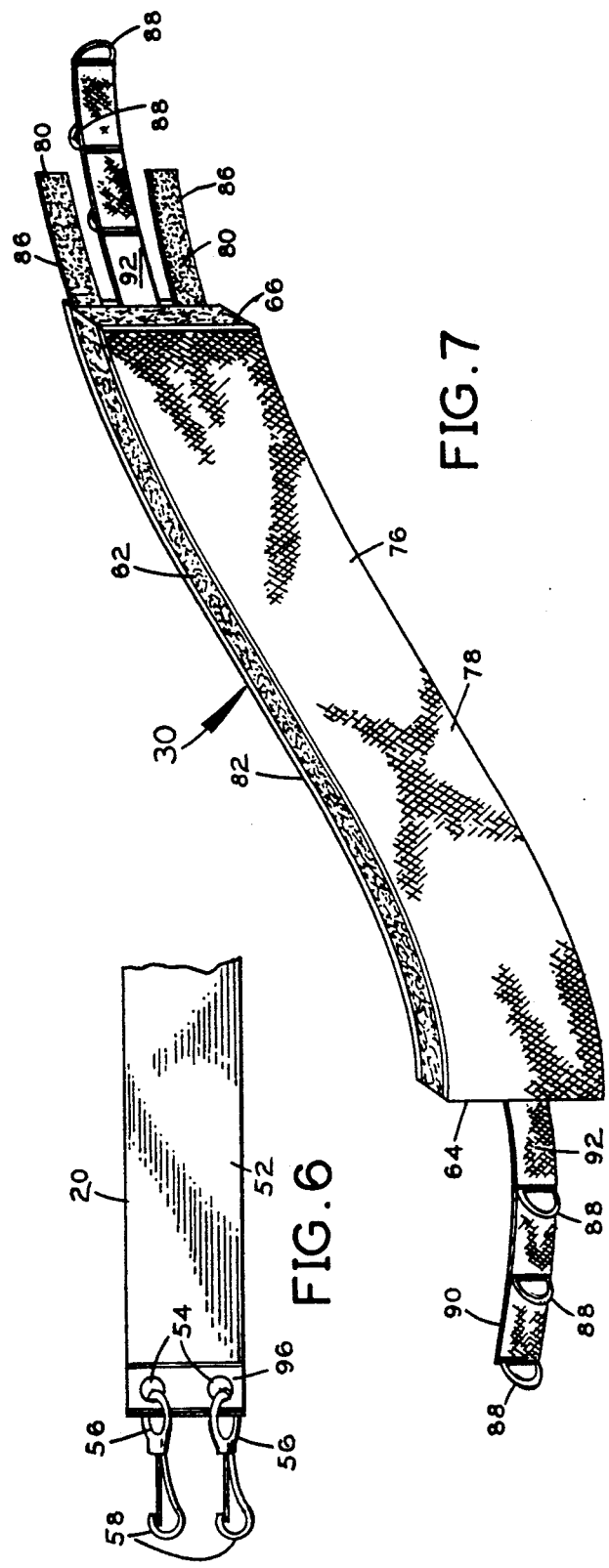

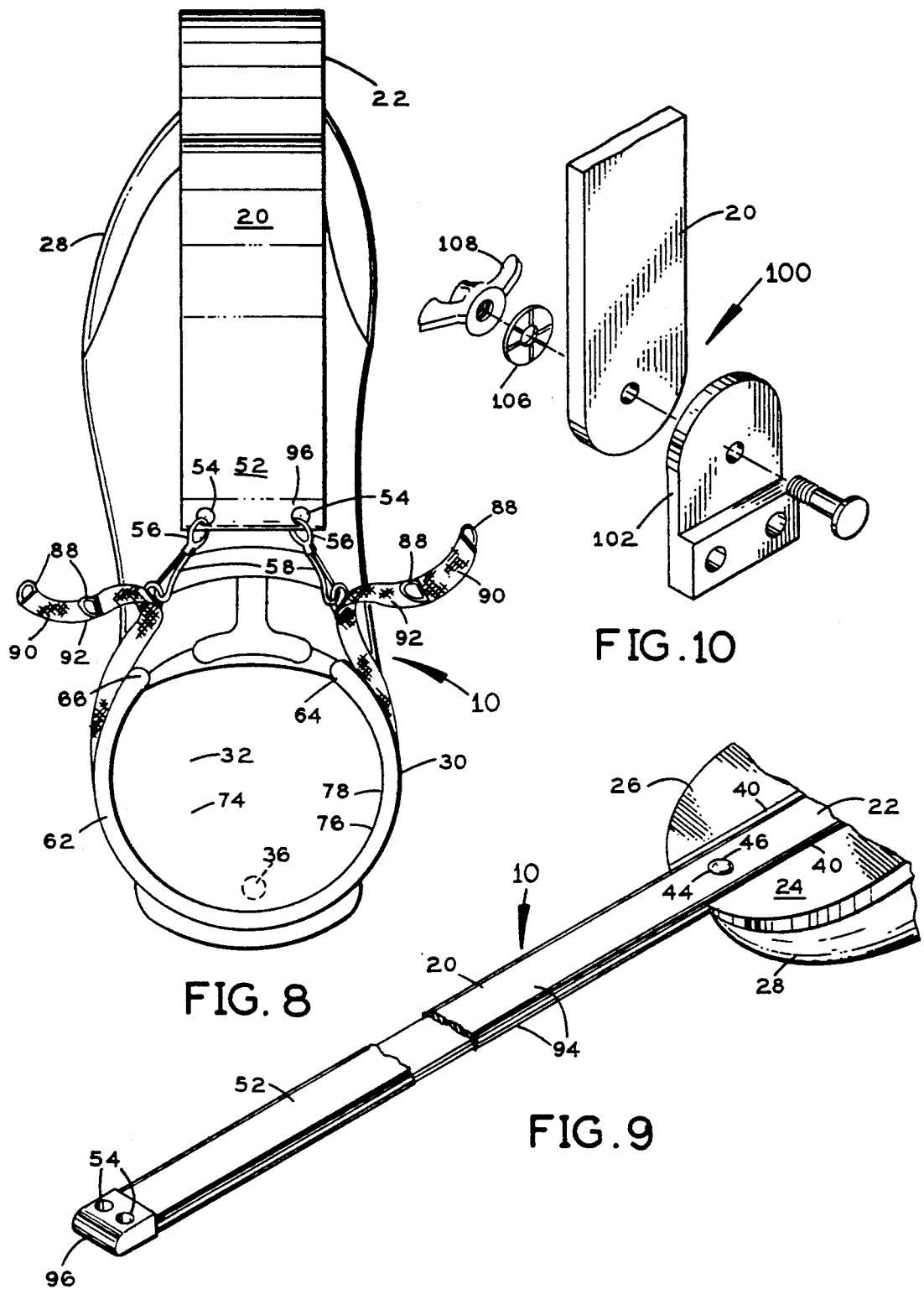

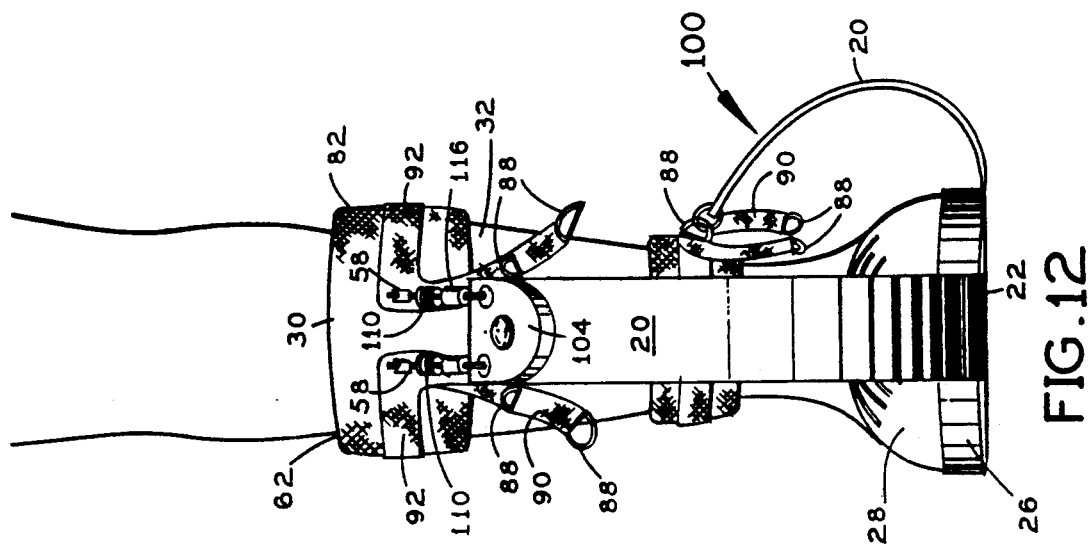
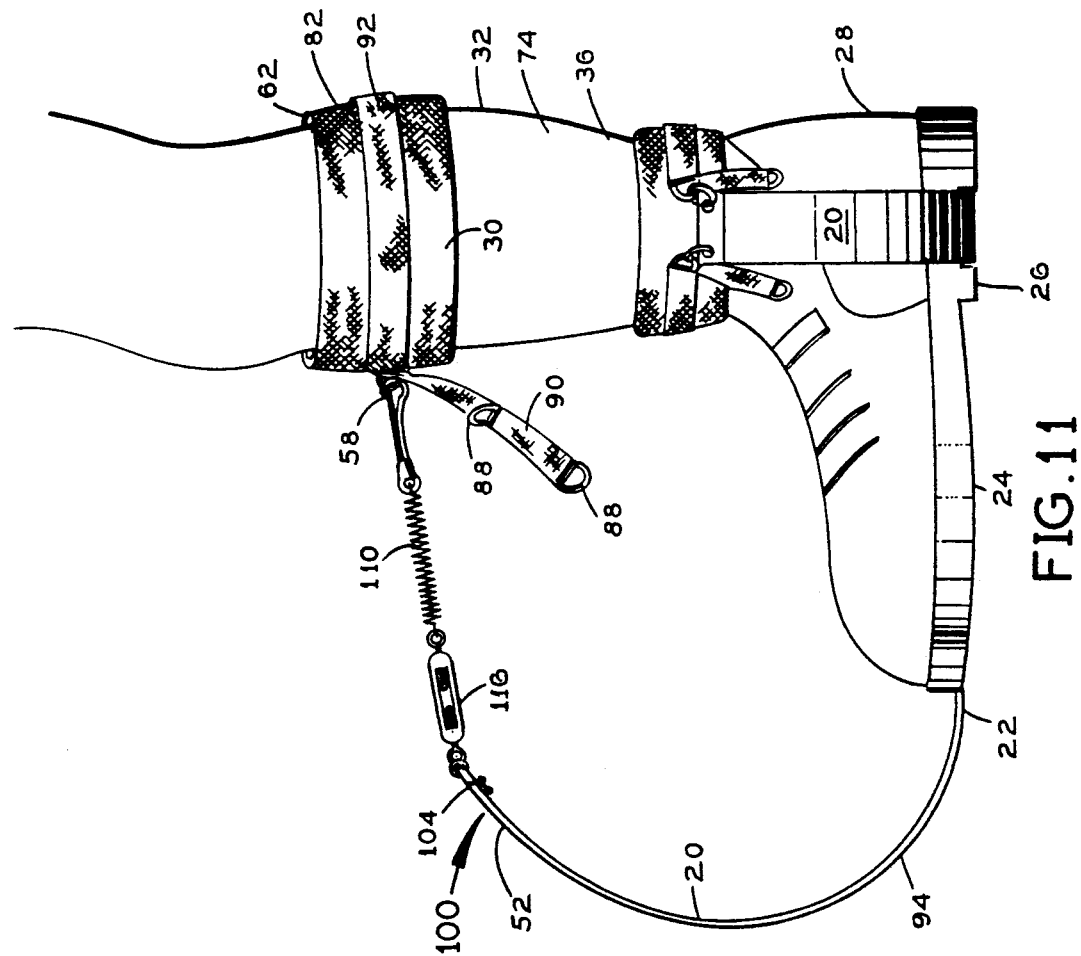

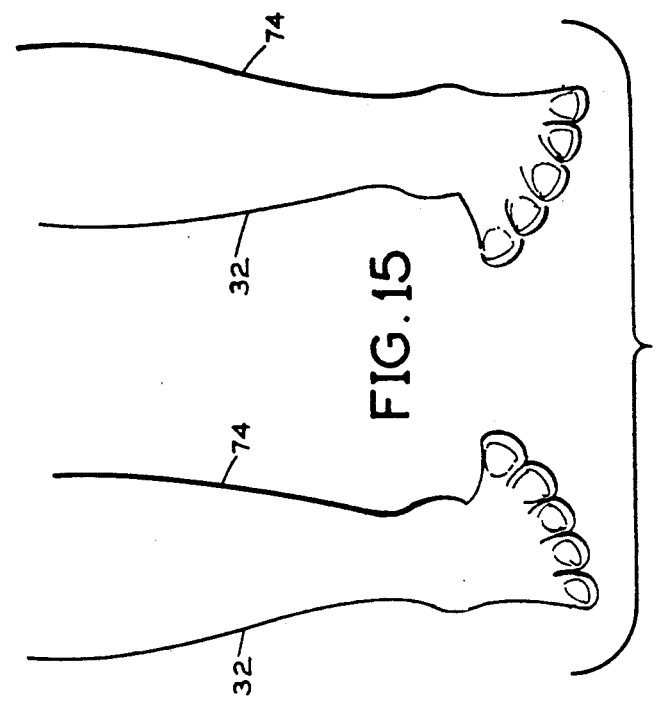
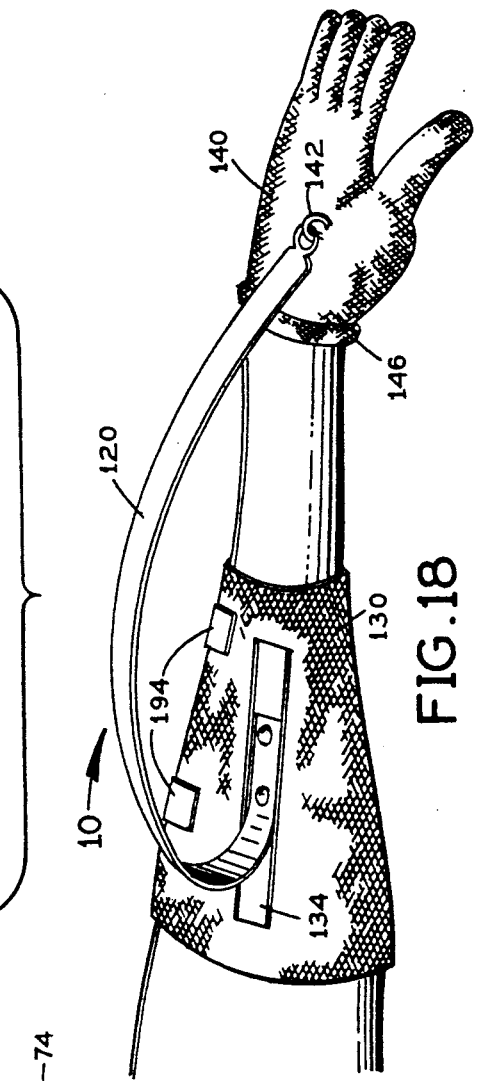
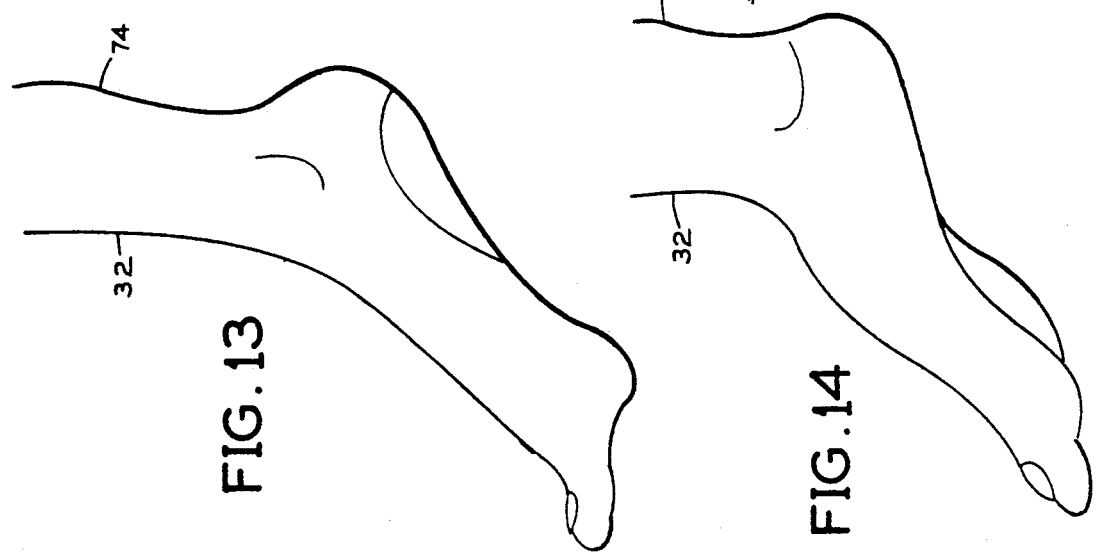

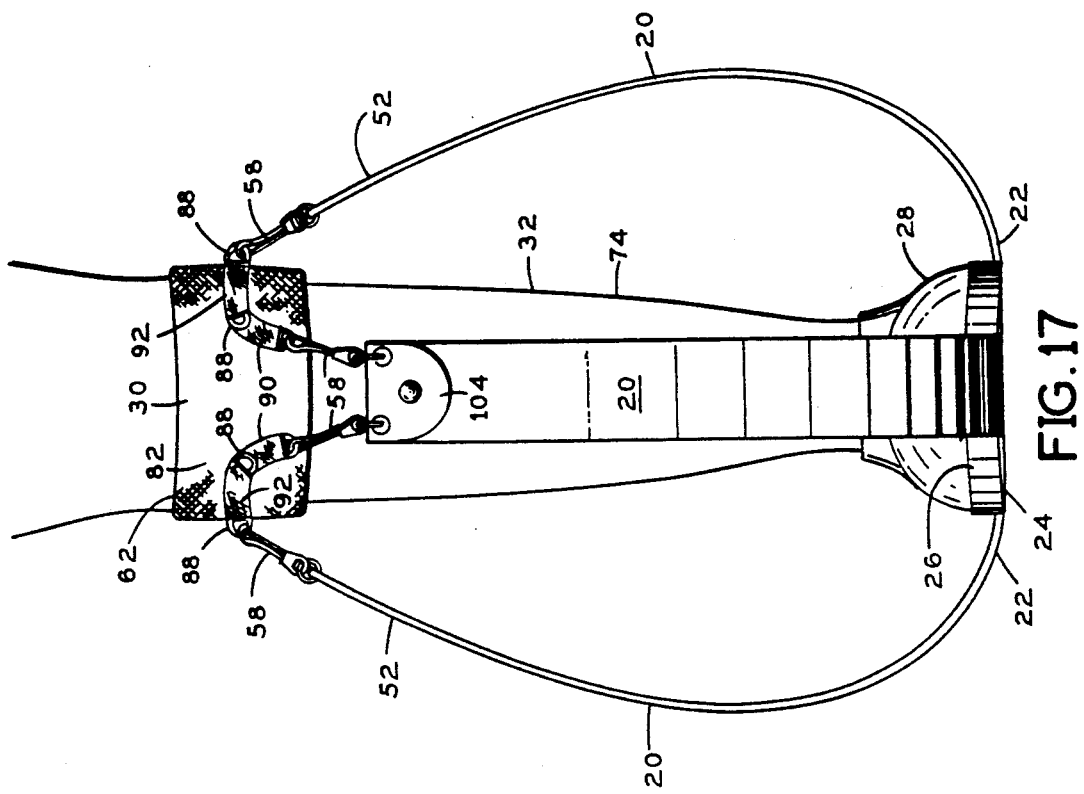
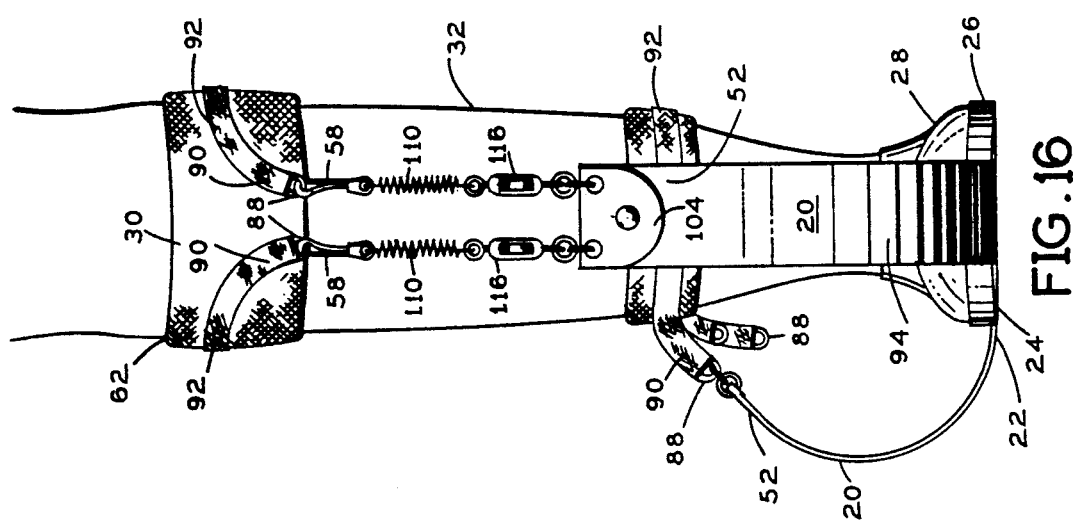

FOOT DROP ORTHOTIC AND GAIT TRAINING DEVICE

BACKGROUND OF THE INVENTION

1. Field of the Invention

The present invention relates generally to the field of appliances for correcting physical disorders such as foot drop and club foot, and more specifically to a resilient strap of plastic or spring steel secured at one end to the bottom of a shoe, extending from the front or side of the shoe and bent upward and back into an arc over the toe or side of the shoe, removably attaching to a harness secured around the lower leg, and exerting a force which tilts the ball of the foot up and toward the knee, thereby progressively stretching the necessary tendon to a length necessary to achieve a normal foot position and gait.

2. Description of the Prior Art

There have long been devices and methods for correcting the pathological contraction of the Achilles' tendon called foot drop and similar maladies. These have included surgery and physical therapy with appliances incorporating elastic bands and rigid casts for positioning the foot in a normal position. Such devices have generally been cumbersome, expensive, excessively painful and marginally effective.

One such prior device is that of Goffredo, U.S. Pat. No. 2,584,010, issued on Jan. 29, 1952. Goffredo teaches a strap which wraps around the ankle and has a loop on its front portion. An elastic cord is fitted through the eyelets of a shoe and through the strap loop and pulled tight enough to raise the foot out of the dropped position. A problem with Goffredo is that the amount of elastic tension which can be generated by a cord narrow enough to fit through a shoe eyelet is minimal. Thus Goffredo essentially just holds the foot up without stretching the achilles tendon and correcting the condition. Another problem is that Goffredo does not prevent the foot from tilting sideways.

Donzelle, U.S. Pat. No. 3,527,202, issued Sep. 8, 1970, presents a mattress and mattress enclosure for housing and providing care for a patient. Tensioned cords can be attached to the apparatus for positioning parts of the body, such as the foot. A problem with Donzelle is that it does not permit a patient to walk while in use, and so is unduly restrictive for a patient being treated only for drop foot. Donzelle is also prohibitively complex and expensive for such a limited treatment.

Schad, U.S. Pat. No. 3,986,501, issued on Oct. 19, 1976, discloses a rigid vertical member which wraps around the back of the calf of the user's leg, from the heel to the knee. A strap joins the top of the member to the leg. An adjustable elastic band extends from the upper portion of the member to the dorsum of a shoe, and hooks through a loop provided there. A problem with Schad is that the shoe and foot can twist to one side so that a proper corrective position is not achieved. Another problem is that elastic bands do not reliably generate steady, strong tension with prolonged use.

Heaney, U.S. Pat. No. 4,329,982, issued on May 18, 1982, reveals a device similar to Schad. One end of an elastic strap is secured to a looped harness encircling the top of the calf. The other end attaches to an off-center loop on the top of the shoe above the toe area. The off-center loop location only enhances the twisting problem of Schad, and the elastic band has the same shortcomings.

Deis, U.S. Pat. No. 4,566,447, issued on Jan. 28, 1986, teaches a device almost identical to Heaney. The Deis device includes a leg band which is secured to the leg just below the knee and an elastic ligament which extends from the leg band to an off-center loop on the toe of the foot or shoe. Deis presents the same problems identified for Heaney.

Marx, U.S. Pat. No. 4,790,300, issued on Dec. 13, 1988, discloses a device for correcting wrist drop. A pivoting rectangular frame is positioned over the top of the hand and attached to a harness mounted on the forearm. The frame is hinged on either side of the wrist and pivots coaxially with the wrist. Cords extend from the frame on either side of the hand and attach to the ends of an elongate member crossing the palm. An elastic member joins the top rear portion of the harness to the frame to pivot the frame upward and pull the hand up into a normal position. A problem with Marx is that the elaborate cantilever frame assembly would be relatively expensive to manufacture. Marx also shares the elastic band problems identified above.

Gyovai, U.S. Pat. No. 4,949,711, issued on Aug. 21, 1990, teaches a joint extension splint for the hand. A cast member is provided around the forearm and wrist and a supports a shaft member extending perpendicularly over the fingers. The shaft member is fitted with a pulley above each finger. A sling wraps around each finger and is attached to a cord which passes over the corresponding pulley and back to an independent coil spring secured to the cast member. In this way each finger is pulled upward and into a desired position. A problem with Gyovai is that it does nothing for wrist drop, but merely lifts the fingers. The cast may hold the wrist in a normal position, but provides no corrective tensioning. Gyovai would also be expensive to manufacture.

Pettine, U.S. Pat. No. 4,955,370, issued on Sep. 11, 1990, reveals a device for rehabilitating the Achilles' tendon following surgery to correct foot drop. A rigid circular loop surrounds the calf and is pivotally connected by two strut members to a shoe support platform. A spring-loaded member connects the front of the platform to the upper portion of one of the strut members. In this way, the front or toe portion of the platform, and of the shoe on the platform, is resiliently lifted up toward the knee of the user. A problem with Pettine is that the frame apparatus is relatively expensive to build. Another problem is that the shoe may slide out of position on the platform.

It is thus an object of the present invention to provide a training appliance which creates a tendon stretching force which can be varied a within a range of tension, and which can be provided with tension force ranges tailored to the needs of a specific patient.

It is another object of the present invention to provide such an appliance which prevents the ankle joint from twisting to one side.

It is still another object of the present invention to provide such an appliance which accomplishes its corrective purpose with a minimum of discomfort.

It is finally an object of the present invention to provide such an appliance which is simple and durable in construction and relatively inexpensive to manufacture.

SUMMARY OF THE INVENTION

The present invention accomplishes the above-stated objectives, as well as others, as may be determined by a fair reading and interpretation of the entire specification.

An appliance is provided for stretching a pathologically contracted Achilles' tendon, including a resilient strap having a first end and a second end, a harness for securing around the leg of a user, a fastener for attaching the first end of the resilient strap to a shoe so that the resilient strap extends out from the shoe, and a fastener for attaching the second end of the resilient strap to the harness so that the resilient strap is bowed against its resilient resistance over the shoe. A channel for receiving the first end of the resilient strap is preferably recessed into the bottom of the shoe. The harness preferably includes a securing strap and a foam rubber pad having an inner surface which rests against the leg of the user and having an outer surface to which the securing strap is attached. The appliance may additionally include a turn buckle for adjusting tension in the strap, a coil spring for preventing the condition known as knee snap, and a direction adjustment assembly for securing the strap relative to the shoe in any of several rotational positions, all linking the strap to the harness. The harness may additionally include nylon fabric attached to the outer surface of the pad, and cotton fabric attached to the inner surface of the pad. The securing strap is preferably fitted with a ring member and the second end of the resilient strap has a clasp which removably engages the ring member. Several ring members are preferably provided on the second end of the resilient strap so that the clasp can engage any one of the ring members to select the desired tension of the resilient strap. A protective coating may optionally be provided around the resilient strap. Also optionally provided is a high friction strip of material sized to fit into the channel for securing over the resilient strap first end to enhance the friction grip between the shoe and the ground. Where the first end is secured in the channel with rivets, an insole pad is provided to protect the user's foot from injurious contact with the rivets.

An appliance is also provided for stretching pathologically contracted wrist tendons, including a resilient strap having a first end and a second end, a harness for securing around the forearm of a user, a glove for placing on the hand of the arm of the user, a fastener for attaching the first end of the resilient strap to the harness so that the resilient strap extends toward the user's shoulder and the second end is bowed back against its resilience over the harness and toward the glove, and a fastener for attaching the second end of the resilient strap to the glove.

BRIEF DESCRIPTION OF THE DRAWINGS

Various other objects, advantages, and features of the invention will become apparent to those skilled in the art from the following discussion taken in conjunction with the following drawings, in which:

FIG. 4 is a bottom view of a shoe with the resilient strap attached with rivets and extending straight forward beyond the toe of the shoe.

FIG. 5 is a side, edge view of the strap of FIG. 4 attached to a sole of a shoe with rivets, and fitted with the high friction strip and the protective insole.

FIG. 6 is a cut-away view of the second end of the resilient strap, showing the perforations, rings, and snap hooks.

FIG. 7 is a perspective view of the harness, showing the foam rubber cushion, the cotton inner lining and nylon outer layer, and the reinforced nylon strap, fitted at each end with three spaced apart D-rings.

FIG. 8 is sectional top view of a foot fitted with the inventive appliance. The engagement of the resilient strap to the harness securing strap is clearly shown.

FIG. 9 is a perspective view of the resilient strap of FIG. 5, covered with the protective layer of foam rubber and a protective plastic sleeve over the second end of the resilient strap.

FIG. 10 is a close-up view of the directional adjustment assembly.

FIG. 11 is a side view of the preferred embodiment with a front-extending strap and the coil spring, turnbuckle and directional adjustment assembly features.

FIG. 12 is a front view of the preferred embodiment with a front-extending strap and the coil spring, turnbuckle and directional adjustment assembly features.

FIG. 13 is an illustration of the pes equinus condition.

FIG. 14 is an illustration of the abnormal plantar flexion condition.

FIG. 15 illustrates the club foot conditions known as pes varus, shown on the left, and pes valgus, shown on the right.

FIG. 16 is a front view of the preferred embodiment having the spring, turnbuckle and directional adjustment features and both front and side mounted straps.

FIG. 17 is a front view of the preferred embodiment having a front mounted strap and two side mounted straps.

FIG. 18 is a perspective view of the second preferred embodiment of the inventive apparatus for correcting drop wrist.

DETAILED DESCRIPTION OF THE PREFERRED EMBODIMENTS

Figure 1:
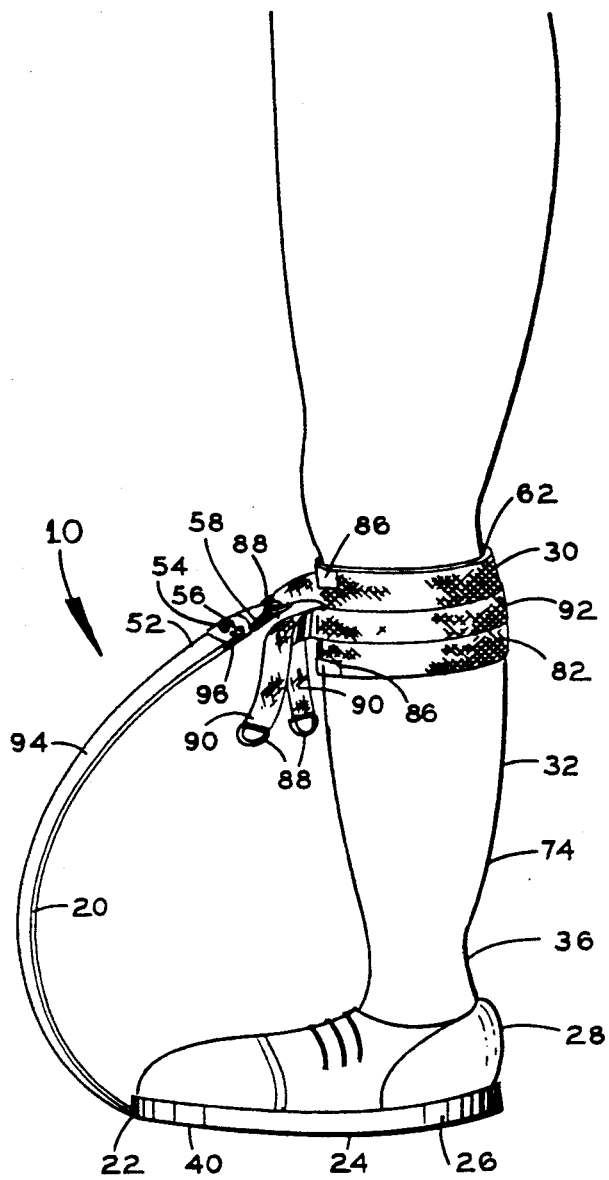
FIG. 1 is a side view of a leg fitted with the inventive appliance.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 2:
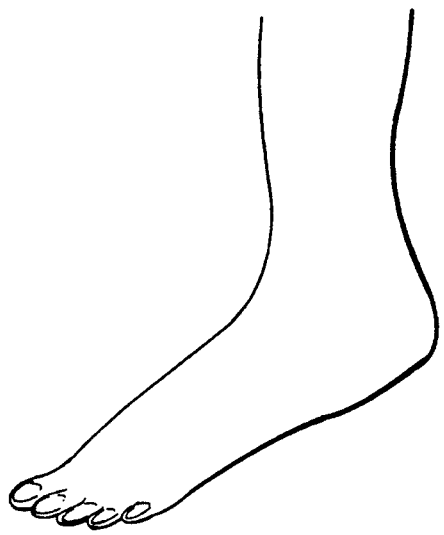
FIG. 2 is a side view of a foot hyper-extended as though afflicted with the condition known as foot drop.
Figure 3:
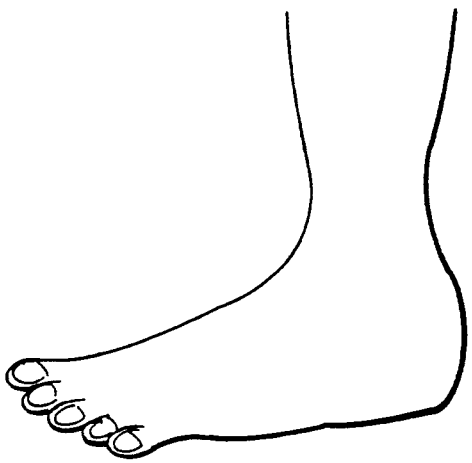
FIG. 3 is a side view of a foot in a normal position.

Referring to FIG. 1, a corrective appliance 10 is disclosed for treating a pathological contraction of the Achilles' tendon. Such a contraction is typically caused by brain or spinal cord damage, disrupting the transmission of nerve impulses to the foot and causing hyperextension of the ball of the foot. This condition is known as foot drop. See FIGS. 2 and 3.

Appliance 10 includes a resilient tensioning strap 20 made of plastic or spring steel secured at one end 22 to the bottom surface 24 of the sole 26 of a shoe 28, preferably extending to the heal area. See FIG. 4. Strap 20 extends out from the front of shoe 26 and bends upward and back over the toe into an arc configuration and removably attaches to a harness 30 secured around the lower leg 32 of the user. See FIG. 1. Strap 20 exerts a force which tilts the ball of the foot up and toward the knee, thereby progressively stretching the Achilles' tendon 36 to a length necessary to achieve a normal foot position.

To secure strap 20 to bottom surface 24 of shoe 28, a channel 40 is cut into the center of sole 26 parallel to the longitudinal axis L of shoe 28. See FIG. 4. The width of channel 40 is slightly larger than the width of strap 20, and the depth of channel 40 is greater than the thickness of strap 20. End 22 of strap 20 fits into channel 40, and is secured with an adhesive or with rivets 44 or both, or with other well known fastening means.

Where rivets 44 are used, they are preferably the flat-head type and are applied from the inside of shoe 28 through sole 26. See FIG. 5. A lock washer (not shown) may optionally surround each rivet 44 inside shoe 28. These lock washers each create a small depression inside shoe 28 which is filled with a rubbery sealing compound such as GOOP TM. They are then covered with a closed washer the size of a penny to protect the user's foot from injury. An innersole is placed over these areas. Several rivets 44 may be placed so close together that they effectively behave as a single fastener and create a single, joint depression. This depression is filled and covered as described above. A spot weld 46 is placed on the protruding end of each rivet stem from underneath shoe 28. Welds 46 are then ground essentially flush with strap 20. To prevent a loss of friction grip between shoe 28 and the ground, a strip 48 of high friction material such as rubber is placed over that portion of strap 20 contained within channel 40. Channel 40 is preferably of a depth sufficient to contain both strap 20 and strip 48 so that strip 48 is essentially flush with bottom surface 24. A protective inner sole is applied over rivet 44 heads inside shoe 28 to shield the user's foot.

The second end 52 of strap 20 is cut off square and has a perforation 54 in each corner. See FIG. 4. Each perforation 54 contains a ring 56 fitted with a snap hook 58. See FIG. 6. Snap hooks 58 engage harness 30. See FIG. 1.

Harness 30 preferably includes a rectangular foam rubber cushion 62, having narrow ends 64 and 66, which wraps around the calf 74 of the user's leg. See FIG. 7. A cotton cloth lining 76 covers the inner surface 78 of cushion 62 and rests against calf 74, increasing comfort and protecting cushion 62. Nylon cloth 72 covers the outer surface 82 of cushion 62 to protect cushion 62 from tearing and abrasion, and to resist moisture. Tabs 86 have hook and loop fasteners 80 such as VELCRO TM and project from nylon cloth 72 at one narrow end 64 of cushion 62 and VELCRO TM patches 78 are located on nylon cloth 72 at the other end of cushion 62. A ribbon 92 of reinforced nylon is sewn to nylon cloth 72 and extends longitudinally along cushion 62 and beyond both of its ends, 64 and 66. Multiple D-shaped rings 88 are periodically sewn to each free protruding end 90 of ribbon 92. See FIG. 8. A snap hook 58 of strap 20 engages one D-shaped ring 88 on each free end 90. The particular D-shaped ring 88 selected determines the tension adjustment of strap 20, because some D-rings 88 are closer than others to calf 74.

Strap 20 is preferably covered with a thin layer 94 of foam rubber and nylon cloth to prevent strap 20 from injuring people and damaging furniture. A plastic sleeve 96 is also provided over second end 52 of strap 20, for the same reasons. See FIG. 9.

Several optional features may be located between strap end 52 and D-shaped rings 88. One is a directional adjustment assembly 100 which includes a rotation plate 102, a round-headed pivot bolt 104 which fits through holes in end 52 and plate 102, a lock washer 106 and a wing nut 108. See FIG. 10. Loosening wing nut 108 permits rotation of end 52, and thus of strap 20, relative to plate 102 to orient the foot in the optimum direction. A coil spring 110 may connect a D-shaped ring 88 either directly to end 52 or to plate 102. See FIGS. 11 and 12. Two parallel springs 110 may be provided. The purpose of spring 110 is to ease or wholly prevent the condition known as knee snap or knee snap-back. Another optional feature is a turnbuckle 116 which may be placed between spring 110 and plate 102. Two parallel turnbuckles 116 may be provided for added strength. See FIGS. 11 and 12. Turnbuckle 116 permits easy and graduated adjustment of the tension of strap 20 applied to the foot. A so-called high-top shoe 28 is preferred for this embodiment to better grasp the foot, and is shown in FIG. 11. These features may be provided on all embodiments described in this application.

Appliance 10 not only stretches the Achilles' tendon but also serves to correct the user's gait, permitting heel to toe walking. It corrects pes equinus, which causes walking on the ball of the foot with the heel off the ground. See FIG. 13. It also corrects abnormal plantar flexion, which results from a shortening of the Achilles' tendon and/or muscles of the lower leg. See FIG. 14.

A strap 20 may be positioned to extend out from and over one or both sides of shoe 28 to correct the club foot conditions known as pes varus and pes vargus. See FIGS. 15 and 16. For this variation, strap 20 is shorter and narrower than the front directed strap 20, and channel 40 is cut perpendicular to the longitudinal axis of shoe 28. The means of strap 20 attachment at either end is as described above. One or more side straps 20 may be combined in the same apparatus 10 with a front strap 20. See FIG. 17. The straps 20 on the sides in FIG. 17 are longer and wider than the side strap 20 of FIG. 12, to maximize access to lower leg 32 and for strength mobilization and to immobilize the leg post-operatively. A low-cut shoe 28 is preferred for this variation to permit maximum access.

Second Preferred Embodiment

A second embodiment of appliance 10 is provided which is designed to correct a condition known as wrist drop, resulting from contracted tendons in the wrist. Similar to foot drop, wrist drop is the pathological flexing of the wrist due to a disruption of nerve impulses from the brain or spinal cord. This condition results from stroke, disease, prolonged bed rest and so forth.

The second embodiment of appliance 10 is essentially like the first, except that harness 130 is sized to fit around the forearm. See FIG. 18. Harness 130 is once again secured with hook and loop type fasteners 194 such as VELCRO TM. Strap 120 is riveted to a steel strip 134 on harness 130 and extends toward the user's shoulder. Then strap 120 bends out and over harness 130 to meet a heavy leather glove 140 fitted on the user's hand, to which strap 120 is secured with a hook and eye fastener 142. Glove 140 has a strap portion 146 for firm anchoring to the hand. The tension in strap 120 pulls the hand into a raised position and thereby correctively stretches the tendons in the wrist.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. An appliance attached to a shoe having a sole for stretching a pathologically contracted Achilles' tendon, comprising:
   a resilient strap having a first end and a second end, said resilient strap extending out from the front of the shoe and bending upward and back over the shoe in an arc configuration;
   harness means for securing around the leg of a user,
   means for attaching said first end of said resilient strap to the sole of the shoe,
   means for attaching said second end of said resilient strap to said harness means such that said resilient strap is bowed against its resilient resistance over said shoe.

2. An appliance according to claim 1, additionally comprising:
   a channel recessed into the bottom of said shoe into which said first end fits, said channel being substantially parallel with said shoe.

3. An appliance according to claim 2, additionally comprising:
   a high friction strip of material sized to fit into said channel for securing over said resilient strap first end to enhance the friction grip between said shoe and the ground.

4. An appliance according to claim 2, wherein said first end is secured in said channel with rivets, additionally comprising:
   an insole pad to protect the user's foot from injurious contact with said rivets.

5. An appliance according to claim 1, wherein said harness means comprises a securing strap and a foam rubber pad having an inner surface which rests against the leg of the user and having an outer surface to which said securing strap is attached.

6. An appliance according to claim 5, wherein said securing strap is fitted with a ring member and said second end of said resilient strap has clasp means which removably engages said ring member.

7. An appliance according to claim 6, wherein a plurality of said ring members are provided on said second end so that said clasp means can engage any one of said ring members to select the desired tension of said resilient strap.

8. An appliance according to claim 5, additionally comprising:
   a protective coating around said resilient strap.

9. An appliance according to claim 5, wherein said harness means additionally comprises nylon fabric attached to said outer surface of said pad, said cotton fabric attached to said inner surface of said pad.

10. An appliance according to claim 1, additionally comprising turn buckle means linking said strap to said harness means, for adjusting tension in said strap.

11. An appliance according to claim 1, additionally comprising coil spring means linking said strap to said harness means, for preventing the condition known as knee snap.

12. An appliance according to claim 1, additionally comprising direction adjustment means for securing said strap relative to said shoe in any of several rotational positions.

* * * * *